United States Patent
Lachmann et al.

(10) Patent No.: US 8,680,032 B2
(45) Date of Patent: *Mar. 25, 2014

(54) COLOR CHANGING CLEANING COMPOSITION

(75) Inventors: Angela Lachmann, Kelkheim am Taunus (DE); Harald Oswald, Hofheim am Taunus (DE); Sambit Roy, Mumbai (IN); Sharmad Chandratre, Mumbai (IN)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,028

(22) PCT Filed: Jul. 15, 2010

(86) PCT No.: PCT/EP2010/004312
§ 371 (c)(1),
(2), (4) Date: Mar. 27, 2012

(87) PCT Pub. No.: WO2011/006658
PCT Pub. Date: Jan. 20, 2011

(65) Prior Publication Data
US 2012/0178662 A1 Jul. 12, 2012

(30) Foreign Application Priority Data
Jul. 17, 2009 (EP) ..................................... 09009318

(51) Int. Cl.
*C11D 3/22* (2006.01)
*C11D 3/40* (2006.01)

(52) U.S. Cl.
USPC ........... 510/146; 510/120; 510/121; 510/143; 510/151; 510/441; 510/445; 510/470; 510/475; 424/491; 424/493; 424/494; 424/498; 424/499; 424/70.13; 424/70.16

(58) Field of Classification Search
USPC ......... 510/120, 121, 143, 146, 151, 441, 445, 510/470, 475; 424/491, 493, 494, 498, 499, 424/70.13, 70.16
See application file for complete search history.

(56) References Cited

U.S. PATENT DOCUMENTS

| | | |
|---|---|---|
| 6,303,564 B1 | 10/2001 | Littau et al. |
| 6,347,637 B1 | 2/2002 | Musha et al. |
| 6,465,411 B2 | 10/2002 | Manske et al. |
| 6,616,770 B2 | 9/2003 | Mushna et al. |
| 6,770,610 B2 | 8/2004 | Takeuchi et al. |
| 6,864,222 B1 | 3/2005 | Manske |
| 6,995,130 B2 | 2/2006 | Manske |
| 7,053,031 B2 | 5/2006 | Jeschke et al. |
| 7,256,169 B2 | 8/2007 | Schimmel et al. |
| 7,632,793 B2 | 12/2009 | Lang |
| 2006/0040835 A1 | 2/2006 | Newkirk et al. |
| 2008/0160084 A1 | 7/2008 | Huynh et al. |
| 2008/0233057 A1* | 9/2008 | Viladot Petit et al. .......... 424/49 |
| 2012/0183479 A1 | 7/2012 | Loffler et al. |

FOREIGN PATENT DOCUMENTS

| | | | |
|---|---|---|---|
| EP | 1222918 | * 7/2002 | ............... A61K 9/50 |
| EP | 1808479 | 7/2007 | |
| WO | WO 2008/132616 | 11/2008 | |

OTHER PUBLICATIONS

PCT International Search Report for PCT/EP 2010/004312, mailed Oct. 28, 2010.
USPTO Office Action for U.S. Appl. No. 13/384,052 mailed Nov. 8, 2012.
Clariant. Texcare SRN. Jul. 2009.
Clariant. Aristoflex TAC. Apr. 2010.
Merriam-Webster. Lactose. http://www.merriam-webster.com/dictionary/lactose.
USPTO Office Action for U.S. Appl. No. 13/384,052 mailed Apr. 11, 2013.

* cited by examiner

*Primary Examiner* — Brian P Mruk
(74) *Attorney, Agent, or Firm* — Anthony A. Bisulca

(57) ABSTRACT

The invention relates to microencapsulated colorant granules consisting of a core (A) and a shell (B), whereby the core (A) has a diameter of between 1 and 1000 micrometer and comprises
a) a colorant (I),
b) microcrystalline cellulose,
c) a polyol;
and whereby the shell (B) has a thickness of between 1 to 500 micrometer and comprises
d) a polymer selected from the group consisting of polycarboxylic acids, vinyl polymers, styrene-(meth)acrylic copolymers, cellulose and cellulose derivatives.
The invention further relates to cleansing compositions, such as hand soaps, containing said microencapsulated colorant granules.

18 Claims, No Drawings

COLOR CHANGING CLEANING COMPOSITION

The present application relates to cleansing compositions comprising color changing materials whereby the color materials are encapsulated.

One of the most effective methods to prevent spread of communicable disease is through effective personal cleaning, particular through accurate (careful) hand washing. Thorough hand cleaning includes washing for a period of time long enough to ensure elimination of microorganisms and attainment of sanitary conditions.

Many soaps and other detergent cleansers can provide the desired levels of hygiene if used correctly. However, these cleansers are usually supplied to the public in bar or liquid form, and people, particularly children, often give only a cursory wash, and therefore do not clean as thoroughly as required to remove dirt, grime and/or disease causing agents.

As such, there is a need to prepare cleaning products that include some sort of indicator for determining how long washing should continue with the product. More particularly, a need currently exists for a cleansing composition that changes color during use for indicating that sufficient time has elapsed and that washing or scrubbing with the product can be stopped. A need exists for a hand soap that indicates a user how much time should be spent washing their hands.

WO 2008/132616 claims a composition comprising at least one thermo chromic dye, changing the color of the cleaning composition when the composition reaches a temperature of about from 21° C. to about 40° C. This color changing cleaning compositions are limited to thermo chromic dyes and do not indicate the period of time for attainment of sanitary conditions.

As such, a need currently exists for a cleaning product that includes some sort of indicator for determining how long washing should continue with the product. More particularly, a need currently exists for a cleansing composition that changes color during use for indicating that sufficient time has elapsed and that washing or scrubbing with the product can discontinue.

It has now been found that pigments, which are converted to particular encapsulated granules are suited to induce color to the foam built up during the washing process.

The present invention relates to microencapsulated colorant granules consisting of a core (A) and a shell (B), whereby the core (A) has a diameter of between 1 and 1000 micrometer, preferably between 10 and 500 micrometer, more preferably between 100 and 400 micrometer, especially preferred between 200 and 300 micrometer, and comprises a) a colorant (I),
b) microcrystalline cellulose,
c) a polyol;

and whereby the shell (B) has a thickness of between 1 to 500 micrometer, preferably between 10 and 400 micrometer, more preferably between 50 and 300 micrometer, especially preferred between 100 and 300 micrometer, and comprises d) a polymer selected from the group consisting of polycarboxylic acids, copolymers of polycarboxylic acids, vinyl polymers, cellulose and cellulose derivatives.

The encapsulated colorant granules according to the present invention can be incorporated in colorless or colored cleansing compositions, preferred hand soaps. During the hand scrubbing processes the shell decomposes and the fine colorant particles are released and disperse into the foam inducing a coloring or color change of the foam. According to the present invention, the coloring or color change of the foam occurs independently of the temperature of the cleansing composition so that there is no need to use thermochromic dyes as colorants. Therefore, it is preferred that colorant (I) and colorant (II) mentioned below are not thermochromic.

In another embodiment of the invention, a white pigment (e), such as titanium dioxide (C.I. Pigment White 6), barium sulfate or zinc oxide, is incorporated into the shell. In this case the color of the core colorant (I) is hidden and the foam is to change from white to the color of colorant (I).

In another embodiment of the invention, the shell contains a colorant (II) (f) which color is different from the color of colorant (I). In this case, it is expedient to apply colorant (II) as a top-coat onto the shell containing components (d) and (e). Then, the color of the foam is to change from the color of colorant (II) to the color of colorant (I). It is preferred the color of colorant (II) being equal or at least similar to the color of the cleansing base, e.g. the soap base, so that the encapsulated colorant granules are invisible or at least hardly visible in the cleansing composition, e.g. soap bar.

In any embodiment of the invention, the core and the shell may contain some water not exceeding an amount for sustaining granular form, e.g. 0 to 50%, preferably 1 to 30%, more preferably 5 to 20%, by weight, based on the total weight of the granules.

Preferably, colorant (I) and colorant (II) are selected from colorants allowed for cosmetic use, such as:

C.I. Pigment Black 7 (C.I. 77266), C.I. Pigment Blue 15 (C.I. 74160), C.I. Pigment Blue 15:1 (C.I. 74160), C.I. Pigment Red 4 (C.I. 12085), C.I. Pigment Red 5 (C.I. 12490), C.I. Pigment Red 112 (C.I. 12370), C.I. Pigment Red 181 (C.I. 73360), C.I. Vat Red 1, C.I. Pigment Green 7 (C.I. 74260), C.I. Pigment Violet 23 (C.I. 51319), C.I. Pigment Yellow 1 (C.I. 11680), C.I. Pigment Yellow 3 (C.I. 11710).

Preferred polyols (c) are glycerine, glycols, polyglycols, pentaerythrite, sugar alcohols, especially mannitol, sorbitol, xylitol, maltitol, lactitol, and monosaccharides, especially lactose.

Microcrystalline cellulose (E460i) and powdered cellulose (E460ii) are commercially available as inactive fillers, thickeners or stabilizers in processed foods and pharmaceuticals. While microcrystalline cellulose is used in the core as component b), powdered cellulose can be used in the shell as component d). Instead of or in addition to powdered cellulose, cellulose derivatives can be used, such as ethyl cellulose, hydroxypropyl cellulose, carboxymethyl cellulose, hydroxypropyl methyl cellulose, hydroxyethyl methyl cellulose, hydroxyethyl cellulose.

Preferred polycarboxylic acids as component d) are polyacrylic acid, polymethacrylic acid, acrylate-methacrylate copolymers, such as methacrylic acid-ethylacrylate copolymers, poly(ethylacrylate-methylmethacrylate-hydroxyethylmethacrylate), styrene-(meth)acrylates, and maleic acid copolymers, such as acrylic acid-maleic acid copolymers.

Preferred vinyl polymers are polyvinyl acetates and vinyl (meth)acrylic copolymers. In a preferred embodiment of the invention the polymer of component d) is selected from the group consisting of polyacrylic acid, polymethacrylic acid, copolymers of polyacrylic and polymethacrylic acid, styrene-(meth)acrylates, maleic acid copolymers, polyvinylacetates, vinyl acrylic copolymers, vinyl methacrylic copolymers, cellulose, ethyl cellulose, hydroxypropyl cellulose, carboxymethyl cellulose, hydroxypropyl methyl cellulose, hydroxyethyl methyl cellulose, and hydroxyethyl cellulose.

The molecular weight of polymers (d) is preferably between 500 and 500 000 g/mol, more preferably between 1 000 and 300 000 g/mol.

In a preferred embodiment, the microencapsulated colorant granules contain
a) 5 to 60% by weight, preferably 10 to 40% by weight, of colorant (I),
b) 10 to 40% by weight, preferably 15 to 30% by weight, of microcrystalline cellulose,
c) 10 to 40% by weight, preferably 15 to 30% by weight, of polyol,
d) 0.1 to 20% by weight, preferably 1 to 10% by weight, of the polymer, relating to the total weight of the granules.

The amount of the white pigment (e) if any, may vary between 0 and 50%, preferably between 0.1 and 30%, by weight, relating to the total weight of the granules.

The amount of colorant (II) (f), if any, may vary between 0 and 25%, preferably between 0.1 and 20% by weight, relating to the total weight of the granules.

In a further preferred embodiment, the microencapsulated colorant granules contain
a) 5 to 60% by weight, preferably 10 to 40% by weight, of colorant (I),
b) 10 to 40% by weight, preferably 15 to 30% by weight, of microcrystalline cellulose,
c) 10 to 40% by weight, preferably 15 to 30% by weight, of polyol,
d) 0.1 to 20% by weight, preferably 1 to 10% by weight, of the polymer,
e) 0.1 to 30% by weight, preferably 1 to 20% by weight, of white pigment;
and 1 to 30%, preferably 5 to 20%, by weight of water, relating to the total weight of the granules.

In a further preferred embodiment, the microencapsulated colorant granules contain
a) 5 to 60% by weight, preferably 10 to 40% by weight, of colorant (I),
b) 10 to 40% by weight, preferably 15 to 30% by weight, of microcrystalline cellulose,
c) 10 to 40% by weight, preferably 15 to 30% by weight, of polyol,
d) 0.1 to 20% by weight, preferably 1 to 10% by weight, of the polymer,
e) 0.1 to 30% by weight, preferably 1 to 20% by weight, of white pigment;
f) 0.1 to 20% by weight, preferably 1 to 15% by weight, of colorant (II); and
1 to 30%, preferably 5 to 20%, by weight of water, relating to the total weight of the granules.

A preferred subject-matter of the present application relates to microencapsulated colorant granules as characterized before, wherein the particle size distribution of the granules is between 100 and 1500 µm, more preferred between 200 and 1000 µm, most preferred between 300 and 600 µm.

A further subject matter of the present application is a process of production of microencapsulated colorant granules as defined before, characterized by the following steps:
admixing and homogenizing water, microcrystalline cellulose, the polyol and the colorant (I) to form a homogeneous mass;
extruding the homogeneous mass followed by granulation and optional drying, to form microbeads as the core of the microencapsulated colorant granules;
coating the microbeads with the components d) and optionally e) and optionally f).

For example, colorant (I) in powderous form is homogenized with microcrystalline cellulose, the polyol and water in a planetary mixer until a homogeneous gel-like mass is obtained. This mass is then subjected to a screw extruder to get small noodles which are further charged into a spherodizer to get microbeads. These microbeads are treated as core. For coating, the core microbeads are subjected to a fluidized bed processing unit, wherein a solution or suspension of components (d) and optionally (e) and optionally (f) in water is sprayed onto the microbeads.

In one embodiment, a suspension of white pigment (e) and polymer (d) in water is sprayed onto the microbeads.

In another embodiment, in a first spraying operation, a suspension of white pigment (e) and polymer (d) in water is sprayed onto the microbeads, followed by a second spraying operation, wherein a suspension of colorant (II) and polymer (d) in water is sprayed onto the microbeads to get a colored coating.

The preferred processing temperature during spraying is between 20 and 80° C., especially between 30 and 60° C.

The coated microbeads obtained are dried to obtain microencapsulated pigment granules according to the invention.

A further subject-matter of the present application relates to a colour changing cleansing composition comprising the microencapsulated colorant granules as described beforehand. In this regard, the present disclosure, in one embodiment, is generally directed to a personal cleansing composition such as a hand soap composition that is intended to change color as the composition is used in order to indicate to a user when a presumably sufficient time of washing has passed, for example 15 seconds to 2 minutes. By changing color as will be described in more detail below, the hand soap composition also educates children and adults about proper hand washing procedures. The visual stimuli not only reinforces proper hygiene habits, but is believed to also encourage children and adults to properly wash their hands.

The hand soap composition of the present disclosure can also be formulated and used in more specific hand scrubbing processes. For example, the hand soap composition of the present disclosure may also be specifically formulated as a surgical or medical hand soap where hand scrubbing is to continue for longer periods of time, such as for periods of time greater than about two minutes, such as from about four minutes to about six minutes.

Although the teachings of the present disclosure are particularly well suited to formulating hand soap compositions, it should be understood that various other cleansing compositions may be made in accordance with the present invention. For instance, other cleansing compositions that may be made in accordance with the present disclosure include shampoos, facial soaps, body washes, baby washes, and pet detergents or washes. Further, other cleansing compositions can also be formulated that may not be intended to wash part of a person's body. For instance, other cleansing compositions that may be made in accordance with the present invention include disinfectants, general purpose cleaners, window cleaners, detergents, vehicle cleaners, or any other suitable cleaning products.

In general, the microencapsulated colorant granules are present in the cleansing composition in an amount from about 0.1% to about 10% by weight, preferably in an amount of 0.2 to about 7% by weight, more preferably in an amount of 0.5 to 5% by weight, relative to the total weight of the cleansing composition.

In a preferred embodiment, the cleansing composition is a hand soap bar.

Cleansing compositions according to the invention contain, besides the soap base, components which are common in the art of soap and cleansing industry, such as nonionic, anionic, cationic, and amphoteric surfactants, suspending agents, emollients, preservatives, fragrances, pH modifiers, anti-microbial agents, colorants, water, and non-aqueous solvents.

The amount of surfactants contained in the cleansing composition can vary greatly depending upon various factors. In some embodiments, the cleansing composition can contain surfactants in an amount from about 1 to about 60% by weight, such as from about 5 to about 40% by weight.

The cleansing composition can also contain various emollients. In fact, some of the above described surfactants may be considered emollients. Particular emollients that may be used include ethoxylated and propoxylated alcohols, such as cetyl alcohols and ethoxylated lanolin.

In some instances, the cleansing composition may also include one or more non-aqueous solvents. Although not required, non-aqueous solvents can sometimes aid in dissolving certain components, e.g., preservatives, anti-microbial agent. Examples of some suitable non-aqueous solvents include, but are not limited to: glycerine; glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Solvent combinations include a glycol, particularly hexylene and/or propylene glycol, and one or more lower alcohols, particularly isopropanol, n-propanol, and/or ethanol.

The cleansing composition can also contain various preservatives to increase the shelf life of the composition. For example, the preservative is present in an amount between about 0.001 to about 5% by weight, in some embodiments between about 0.001 to about 1% by weight, and in some embodiments, between about 0.1 to about 0.15% by weight of the cleansing formulation.

If necessary, various pH modifiers may be utilized in the cleansing composition to achieve the desired pH level. For instance, some examples of basic pH modifiers that may be used in the present disclosure include, but are not limited to ammonia, mono-, di-, and tri-alkylamines, mono-, di-, and tri-alkanolamines, alkali metal and alkaline earth metal hydroxides, alkali metal and alkaline earth metal silicates, mineral acids, carboxylic acids, and polymeric acids.

Suspending agents may comprise a clay, a starch including starch derivatives, a modified cellulose, a natural gum, a wax, a fatty acid, a fatty alcohol, a multifunctional alcohol, colloidal or fumed particles, a fatty acid ester, a polyoxyethylene glycol ether, or mixtures thereof.

The suspending agent may be present in the cleansing composition in an amount sufficient to prevent the encapsulated pigment granules from settling. The suspending agent may be present in the cleansing composition in an amount from about 0.1 to about 15% by weight, such as from about 0.1 to about 10% by weight. For example, a laponite clay is present as a suspending agent in an amount from about 0.5 to about 3% by weight.

The colour changing cleansing composition of the invention can be prepared by the following process steps comprising preparing a soap base including components which are common in the art of soap and cleansing industry as defined above, blending said soap base, the encapsulated microbeads and, optionally, further components which are common in the art of soap and cleansing industry as defined above, in a mixing device, e.g. a Sigma mixer, at a temperature of about 20 to 40° C., mixing in rolling mills at a temperature of about 20 to 40° C. until a homogeneous mass is obtained, then extruding the homogeneous mixture at a temperature of about 30 to 60° C., and optionally cutting into bar-sized units.

In the following examples "parts" refer to parts by weight and percentages refer to weight percent.

EXAMPLES

Example 1

Encapsulated Pigment Granules (Colorant (I))

33 parts of powdered C.I. Pigment Red 181 were homogenized with 33 parts of microcrystalline cellulose and 33 parts of lactose and 30 parts of water in a planetary mixer until a homogeneous gel-like mass was obtained. This mass was subjected to a screw extruder to get small noodles which were further charged into a spherodizer to get microbeads of about 200 to 300 micrometer in diameter. The microbeads were subjected to a fluidized bed processing unit. A dispersion of 5 parts of methacrylic acid-ethylacrylate copolymer (1:1; mw approx. 250 000 g/mol) in 5 parts of water was sprayed with the microbeads at a temperature of about 50° C. to get a colorless polyacrylate coating onto the beads. The final beads were removed from the fluidized bed unit and dried.

Example 2

Encapsulated Pigment Granules (Colorant (I)+$TiO_2$)

33 parts of powdered C.I. Pigment Blue 15:1 were homogenized with 33 parts of microcrystalline cellulose and 33 parts of xylitol and 30 parts of water in a planetary mixer until a homogeneous gel-like mass was obtained. This mass was subjected to a screw extruder to get small noodles which were further charged into a spherodizer to get microbeads of about 200 to 250 micrometer in diameter. These microbeads were treated as core.

The microbeads were subjected to a fluidized bed processing unit. A dispersion of 15 parts of titanium dioxide in 5 parts of water and 5 parts of sodium polyacrylate (Mowilith® DM 6400) was sprayed with the microbeads at a temperature of about 50° C. to get a $TiO_2$-polyacrylate coating onto the beads. The final beads were removed from the fluidized bed unit and dried to give encapsulated pigment granules of about 400 to 450 micrometer in diameter.

Example 3

Encapsulated Pigment Granules (Colorant (I)+$TiO_2$+Colorant (II))

33 parts of powdered C.I. Pigment Green 7 were homogenized with 33 parts of microcrystalline cellulose and 33 parts of sorbitol and 30 parts of water in a planetary mixer until a homogeneous gel-like mass was obtained. This mass was subjected to a screw extruder to get small noodles which were further charged into a spherodizer to get microbeads of about 200 to 250 micrometer in diameter. These microbeads were treated as core.

The microbeads were subjected to a fluidized bed processing unit. A dispersion of 15 parts of titanium dioxide in 5 parts of water and 5 parts of sodium polyacrylate (Mowilith® DM 6400) was sprayed with the microbeads at a temperature of about 50° C. to get a $TiO_2$-polyacrylate coating onto the beads.

Further, a suspension of 15 parts of C.I. Pigment Red 5, 5 parts of water and 5 parts of sodium polyacrylate (Mowilith®

DM 6400) was sprayed with the coated microbeads at a temperature of about 50° C. to get a red-colored coating on these beads.

The final beads were removed from the fluidized bed unit and dried to give encapsulated pigment granules of about 400 to 450 micrometer in diameter.

Application Example. Cleansing Composition

A soap base containing the following ingredients was provided:

| |
|---|
| 70 parts dry palm oil soap base noodles, |
| 1 part citric acid, |
| 1 part disodium EDTA, |
| 1 part $TiO_2$; |
| 1 part perfume; |
| 5 part talcum; |
| 5 part emulsifier; |
| 3 part C.I. Pigment Red 5; |
| 3 parts glycerine; |
| 10 parts water. |

100 parts of the above soap base were blended with 3 parts of microbeads of Example 1, 2 or 3 in a Sigma mixer, at a temperature of about 30° C., for 45 minutes, the resulting mass transferred into a rolling mill apparatus, mixed therein at a temperature of about 30° C. until a homogeneous mass was obtained, then transferred to an extruder, extruding the mixture at a temperature of about 50° C. to make soap in cylindrical tube, and cut into bar-sized units.

In a hand-washing test with water (25-30° C.), color change of the foam occurred after about 2 minutes.

The invention claimed is:

1. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   and wherein the shell (b) further comprises a white pigment (e).

2. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   and wherein the shell further comprises (f) a colorant (II).

3. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   wherein the shell includes a white pigment (e), and wherein the colorant granules further includes
   e) 0.1 to 30% by weight of white pigment; and 1 to 30% by weight of water, and includes
   a) 5 to 60% by weight of colorant (I),
   b) 10 to 40% by weight of microcrystalline cellulose,
   c) 10 to 40% by weight of polyol,
   d) 0.1 to 20% by weight of the polymer,
   relating to the total weight of the granules.

4. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   wherein the shell includes a colorant (II) and a white pigment (e), further comprising
   e) 0.1 to 30% by weight of white pigment;
   f) 0.1 to 20% by weight of colorant (II); and 1 to 30% by weight of water, and comprising
   a) 5 to 60% by weight of colorant (I),
   b) 10 to 40% by weight of microcrystalline cellulose,
   c) 10 to 40% by weight of polyol,
   d) 0.1 to 20% by weight of the polymer,
   relating to the total weight of the granules.

5. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   wherein the shell contains a colorant (II) and wherein colorant (I) and colorant (II) are colorants allowed for cosmetic use.

6. Microencapsulated colorant granules consisting of a core (A) and a shell (B), whereby the core (A) has a diameter of between 1 and 1000 micrometer and comprises
   a) a colorant (I),
   b) microcrystalline cellulose,
   c) a polyol;
   and whereby the shell (B) has a thickness of between 1 to 500 micrometer and comprises
   d) a polymer selected from the group consisting of polycarboxylic acids, copolymers of polycarboxylic acids, vinyl polymers, cellulose and cellulose derivatives,
   wherein the shell contains a colorant (II) and
   wherein colorant (I) and colorant (II) are selected from the group consisting of C.I. Pigment Black 7, C.I. Pigment Blue 15, C.I. Pigment Blue 15:1, C.I. Pigment Red 4, C.I. Pigment Red 5, C.I. Pigment Red 112, C.I. Pigment Red 181, C.I. Vat Red 1, C.I. Pigment Green 7, C.I. Pigment Violet 23, C.I. Pigment Yellow 1, and C.I. Pigment Yellow 3.

7. Microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives,
 wherein the shell contains a white pigment (e) and
 wherein the polyol (c) is selected from the group consisting of glycerine, glycols, polyglycols, pentaerythrite, sugar alcohols, sorbitol, xylitol, maltitol, lactitol, and monosaccharides.

8. Microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polyacrylic acid, polymethacrylic acid, copolymers of polyacrylic acid, copolymers of polymethacrylic acid, styrene-(meth)acrylates, maleic acid copolymers, polyvinylacetates, vinyl acrylic copolymers, vinyl methacrylic copolymers, cellulose, ethyl cellulose, hydroxypropyl cellulose, carboxymethyl cellulose, hydroxypropyl methyl cellulose, hydroxyethyl methyl cellulose, and hydroxyethyl cellulose, and
 wherein the shell (b) contains a white pigment (e).

9. A process for manufacturing microencapsulated colorant granules) consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives;
 wherein the shell optionally includes a white pigment (e) and optionally (f) a colorant (II),
 comprising the steps of:
  admixing and homogenizing water, microcrystalline cellulose, the polyol and the colorant (I) to form a homogeneous mass;
  extruding the homogeneous mass followed by granulation and optional drying, to form microbeads as the core of the microencapsulated colorant granules;
  coating the microbeads with the components d) and optionally e) and optionally f).

10. A color changing cleansing composition comprising microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives, and
 wherein the shell includes a white pigment (e).

11. A hand soap comprising microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives, and
 wherein the shell (b) contains a white pigment (e).

12. A cleansing composition comprising microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives, and
 wherein the shell includes a white pigment (e), and
 wherein the microencapsulated colorant granules are present in an amount of 0.1 to 10% by weight, relative to the total weight of the cleansing composition.

13. Microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives, and
 wherein the polyol (c) is selected from the group consisting of mannitol and lactose.

14. Microencapsulated colorant granules consisting of a core (A) and a shell (B), whereby the core (A) has a diameter of between 1 and 1000 micrometer and comprises
 a) a colorant (I),
 b) microcrystalline cellulose,
 c) a polyol;
 and whereby the shell (B) has a thickness of between 1 to 500 micrometer and comprises
 d) a polymer selected from the group consisting of polycarboxylic acids, copolymers of polycarboxylic acids, vinyl polymers, cellulose and cellulose derivatives,
 wherein the shell contains a colorant (II), and
 wherein the polyol (c) is selected from the group consisting of glycerine, glycols, polyglycols, pentaerythrite, sugar alcohols, sorbitol, xylitol, maltitol, lactitol, and monosaccharides.

15. Microencapsulated colorant granules consisting of a core (A) and a shell (B), whereby the core (A) has a diameter of between 1 and 1000 micrometer and comprises a) a colorant (I), b) microcrystalline cellulose, c) a polyol;

and whereby the shell (B) has a thickness of between 1 to 500 micrometer and comprises d) a polymer selected from the group consisting of polyacrylic acid, polymethacrylic acid, copolymers of polyacrylic acid, copolymers of copolymers, polymethacrylic acid, styrene-(meth)acrylates, maleic acid copolymers, polyvinylacetates, vinyl acrylic copolymers, vinyl methacrylic copolymers, cellulose, ethyl cellulose, hydroxypropyl cellulose, carboxymethyl cellulose, hydroxypropyl methyl cellulose, hydroxyethyl methyl cellulose, and hydroxyethyl cellulose, and wherein the shell contains a colorant (II).

16. A color changing cleansing composition comprising microencapsulated colorant granules consisting of a core (A) and a shell (B), whereby the core (A) has a diameter of between 1 and 1000 micrometer and comprises a) a colorant (I), b) microcrystalline cellulose, c) a polyol;

and whereby the shell (B) has a thickness of between 1 to 500 micrometer and comprises d) a polymer selected from the group consisting of polycarboxylic acids, copolymers of polycarboxylic acids, vinyl polymers, cellulose and cellulose derivatives, and wherein the shell includes a colorant (II).

17. A hand soap comprising microencapsulated colorant granules consisting of a core (A) and a shell (B), whereby the core (A) has a diameter of between 1 and 1000 micrometer and comprises a) a colorant (I), b) microcrystalline cellulose, c) a polyol;

and whereby the shell (B) has a thickness of between 1 to 500 micrometer and comprises d) a polymer selected from the group consisting of polycarboxylic acids, copolymers of polycarboxylic acids, vinyl polymers, cellulose and cellulose derivatives, and wherein the shell (b) contains a colorant (II).

18. A cleansing composition comprising microencapsulated colorant granules consisting of a core (A) and a shell (B), whereby the core (A) has a diameter of between 1 and 1000 micrometer and comprises a) a colorant (I), b) microcrystalline cellulose, c) a polyol;

and whereby the shell (B) has a thickness of between 1 to 500 micrometer and comprises d) a polymer selected from the group consisting of polycarboxylic acids, copolymers of polycarboxylic acids, vinyl polymers, cellulose and cellulose derivatives, and wherein the shell includes a colorant (II), and wherein the microencapsulated colorant granules are present in an amount of 0.1 to 10% by weight, relative to the total weight of the cleansing composition.

* * * * *